United States Patent [19]
Sancoff et al.

[11] Patent Number: 5,578,005
[45] Date of Patent: Nov. 26, 1996

[54] APPARATUS AND METHODS FOR MULTIPLE FLUID INFUSION

[75] Inventors: Gregory E. Sancoff, Windham, N.H.; Mark C. Doyle, San Diego; Frederic P. Field, Solana Beach, both of Calif.

[73] Assignee: River Medical, Inc., San Diego, Calif.

[21] Appl. No.: 307,504

[22] Filed: Sep. 16, 1994

Related U.S. Application Data

[63] Continuation-in-part of Ser. No. 105,284, Aug. 6, 1993, Pat. No. 5,397,303, and Ser. No. 105,327, Aug. 6, 1993, Pat. No. 5,398,851.

[51] Int. Cl.⁶ .................................................. A61M 37/00
[52] U.S. Cl. ...................... 604/82; 604/132; 604/141; 128/DIG. 12; 222/399
[58] Field of Search ...................... 604/82, 81, 65–67, 604/135–139, 132, 133, 140–143, 89–92; 222/386.5, 394, 395, 399; 128/DIG. 12, DIG. 24

[56] References Cited

U.S. PATENT DOCUMENTS

| | | |
|---|---|---|
| 754,037 | 3/1904 | Anderson . |
| 1,469,501 | 10/1923 | Dollin . |
| 1,832,817 | 11/1931 | Pearsons . |
| 2,105,690 | 1/1938 | Greenblatt . |
| 2,381,749 | 8/1945 | Hull et al. . |
| 2,473,912 | 6/1949 | Schwinn . |
| 2,845,090 | 7/1958 | Rost . |
| 2,912,018 | 11/1959 | Leech . |
| 3,023,750 | 3/1962 | Baron . |
| 3,053,422 | 9/1962 | Tenison et al. . |
| 3,122,181 | 2/1964 | Hebenstreit et al. . |
| 3,153,414 | 10/1964 | Beall et al. . |
| 3,178,075 | 4/1965 | Riedl et al. . |
| 3,217,947 | 11/1965 | Bauerlein . |
| 3,357,601 | 12/1967 | Crawford et al. . |
| 3,367,545 | 2/1968 | Cook . |
| 3,384,113 | 5/1968 | Pennisi . |
| 3,385,481 | 5/1968 | Frangos . |
| 3,405,845 | 10/1968 | Cook . |
| 3,468,308 | 9/1969 | Bierman . |
| 3,585,982 | 6/1971 | Hollinshead . |
| 3,595,467 | 7/1971 | Goglio . |
| 3,640,277 | 2/1972 | Adelberg . |
| 3,662,929 | 5/1972 | Sims . |
| 3,667,652 | 6/1972 | Morane et al. . |
| 3,708,089 | 1/1973 | Holder . |
| 3,718,236 | 2/1973 | Reyner et al. . |
| 3,739,947 | 6/1973 | Baumann et al. . |
| 3,840,009 | 10/1974 | Michaels et al. . |
| 3,894,538 | 7/1975 | Richter . |
| 3,949,911 | 4/1976 | Morane . |
| 4,043,489 | 8/1977 | Buckman . |
| 4,049,158 | 9/1977 | Lo et al. . |
| 4,111,613 | 9/1978 | Sperry . |
| 4,203,441 | 5/1980 | Theeuwes . |
| 4,222,127 | 9/1980 | Donachy . |
| 4,235,236 | 11/1980 | Theeuwes . |
| 4,237,881 | 12/1980 | Beigler et al. . |
| 4,331,728 | 5/1982 | Theeuwes . |
| 4,335,835 | 6/1982 | Beigler . |

(List continued on next page.)

FOREIGN PATENT DOCUMENTS

WO9325269  12/1993  WIPO .

*Primary Examiner*—John D. Yasko
*Attorney, Agent, or Firm*—Knobbe, Martens, Olson & Bear

[57] ABSTRACT

We disclose apparatus and methods for delivering for patient infusion or other use two or more fluids either sequentially or simultaneously. The apparatus has a fluid delivery compartment containing a first infusion fluid, a flexible membrane, and an openable bag containing a second infusion fluid. An attached gas reaction compartment contains chemical reactants which, when combined, react to evolve gas. The gas expands a gas expansion chamber causing the membrane to move into the fluid delivery compartment, displacing the first infusion fluid. The membrane eventually contacts and compresses the openable bag. Pressure from the membrane causes the bag to open and discharge its contents out of the infusion device.

23 Claims, 6 Drawing Sheets

U.S. PATENT DOCUMENTS

| | | |
|---|---|---|
| 4,360,131 | 11/1982 | Reyner . |
| 4,373,341 | 2/1983 | Mahaffy et al. . |
| 4,376,500 | 3/1983 | Banks et al. . |
| 4,379,453 | 4/1983 | Baron . |
| 4,410,321 | 10/1983 | Pearson et al. . |
| 4,468,220 | 8/1984 | Willbanks . |
| 4,478,044 | 10/1984 | Magid . |
| 4,491,250 | 1/1985 | Liebermann . |
| 4,507,116 | 3/1985 | Leibinsohn . |
| 4,510,734 | 4/1985 | Banks et al. . |
| 4,511,355 | 4/1985 | Franetzki . |
| 4,513,884 | 4/1985 | Magid . |
| 4,518,103 | 5/1985 | Lim et al. . |
| 4,553,685 | 11/1985 | Magid . |
| 4,567,948 | 2/1986 | Rozniecki . |
| 4,640,445 | 2/1987 | Yamada . |
| 4,646,946 | 3/1987 | Reyner . |
| 4,648,955 | 3/1987 | Maget . |
| 4,673,392 | 6/1987 | Keime . |
| 4,675,020 | 6/1987 | McPhee . |
| 4,679,706 | 7/1987 | Magid et al. . |
| 4,687,423 | 8/1987 | Maget et al. . |
| 4,802,343 | 2/1989 | Rudick . |
| 4,804,366 | 2/1989 | Zdeb et al. . |
| 4,838,856 | 6/1989 | Mulreany et al. ........................ 604/65 |
| 4,847,093 | 7/1989 | Ayer . |
| 4,850,978 | 7/1989 | Dudar et al. . |
| 4,870,805 | 10/1989 | Morane . |
| 4,886,514 | 12/1989 | Maget . |
| 4,893,730 | 1/1990 | Bolduc . |
| 4,896,794 | 1/1990 | Banks et al. . |
| 4,898,209 | 2/1990 | Zbed . |
| 4,902,278 | 2/1990 | Maget et al. . |
| 4,923,095 | 5/1990 | Dorfman et al. . |
| 4,936,829 | 6/1990 | Zdeb et al. . |
| 4,946,439 | 8/1990 | Eggers ................................ 604/81 X |
| 5,009,340 | 4/1991 | Morane . |
| 5,022,564 | 6/1991 | Reyner . |
| 5,024,657 | 6/1991 | Needham et al. . |
| 5,032,619 | 7/1991 | Frutin et al. . |
| 5,035,351 | 7/1991 | Moran . |
| 5,049,129 | 9/1991 | Zdeb et al. . |
| 5,054,651 | 10/1991 | Morane . |
| 5,080,652 | 1/1992 | Sancoff et al. . |
| 5,090,963 | 2/1992 | Gross . |
| 5,106,374 | 4/1992 | Apperson et al. . |
| 5,116,316 | 5/1992 | Sertic et al. . |
| 5,133,701 | 7/1992 | Han . |
| 5,137,186 | 8/1992 | Moran . |
| 5,167,631 | 12/1992 | Thompson et al. . |
| 5,179,982 | 1/1993 | Bérubé et al. . |
| 5,219,331 | 6/1993 | Vanderveen ................................ 604/81 |
| 5,301,851 | 4/1994 | Frutin . |
| 5,333,763 | 8/1994 | Lane et al. . |
| 5,398,851 | 3/1995 | Sancoff et al. ........................ 604/81 X |

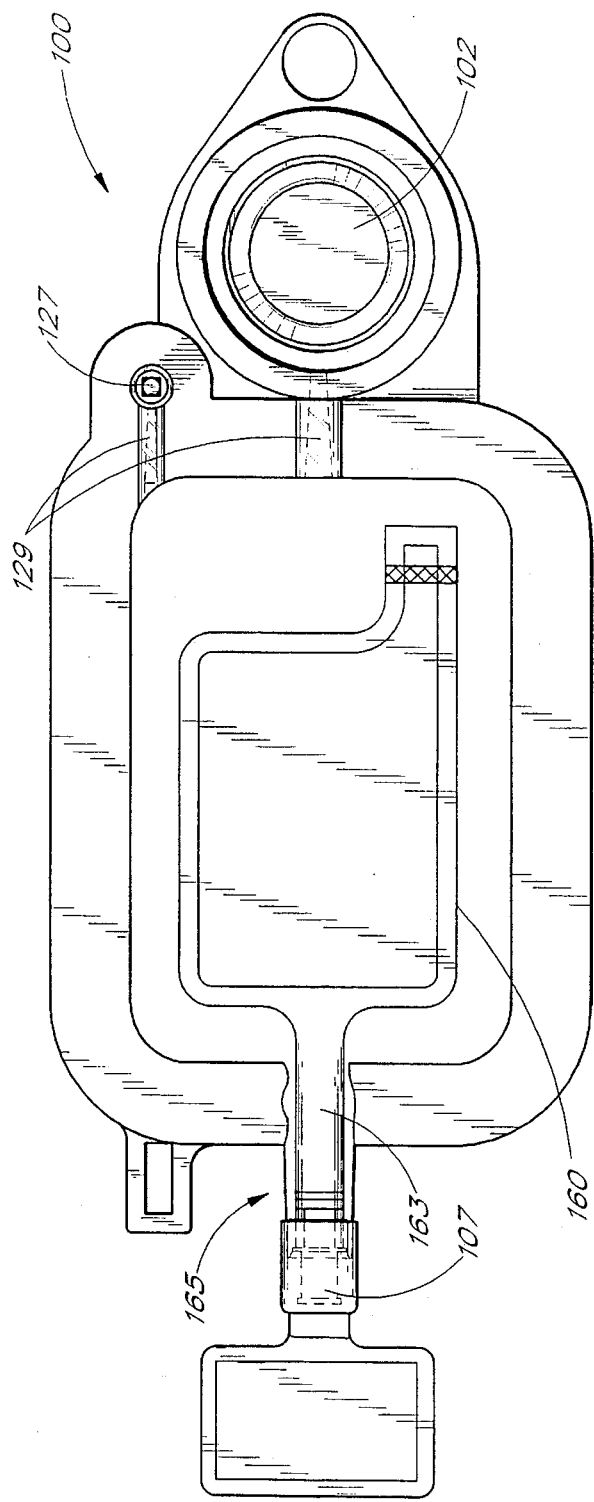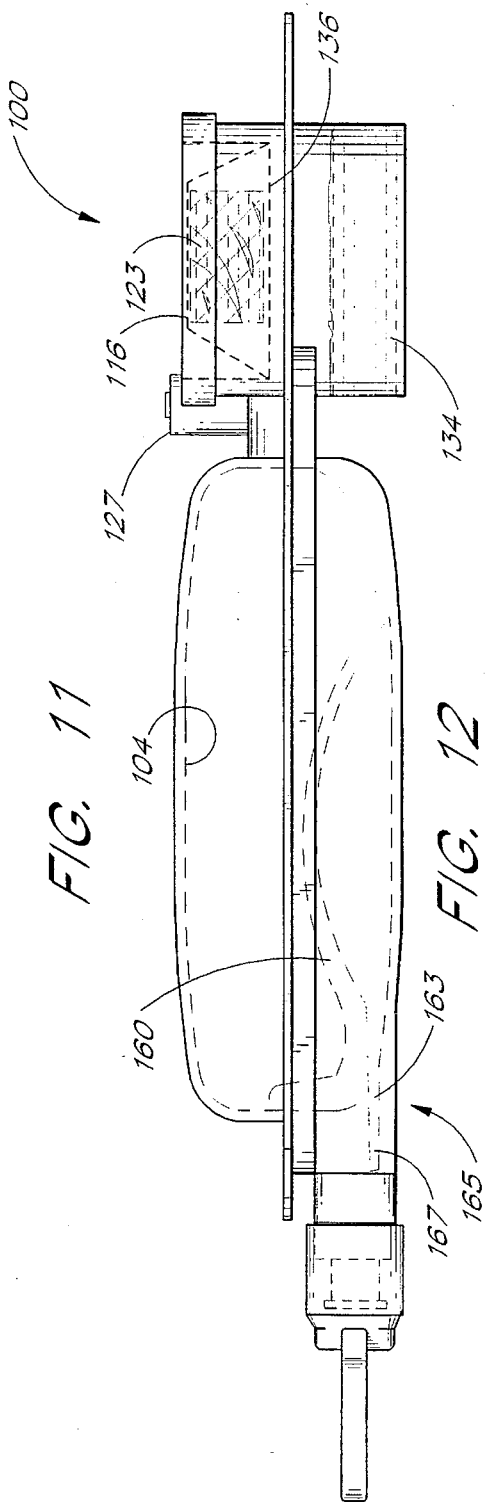

APPARATUS AND METHODS FOR MULTIPLE FLUID INFUSION

CROSS REFERENCE TO RELATED APPLICATIONS

This application is a continuation-in-part application of U.S. patent applications, Ser. Nos. 08/105,284 filed Aug. 6, 1993, now U.S. Pat. No. 5,397,303 and 08/105,327, filed Aug. 6, 1993, now U.S. Pat. No. 5,398,851, the disclosures of which we incorporate here by reference.

BACKGROUND OF THE INVENTION

1. Field of the Invention

This invention relates to apparatus and methods to provide delivery of two or more fluids from an infusion pump.

2. Background of the Prior Art

The controlled delivery of liquids, particularly those containing medications, to patients has received substantial attention in the medical arts. The purpose of drug infusion is to give a patient medication intravenously over a known, usually prolonged, time period. Infusion eliminates the need for repeated injections and reduces the risk that the patient will develop drug sensitivities. Moreover, it is widely believed that sustained treatment with a drug is generally more effective than a single bolus treatment. Further, infusion pump devices allow for ambulatory treatment of a patient, i.e., the patient need not be attached to an intravascular ("IV") stand and bag.

There is often a need for infusion devices to deliver two or more fluidsto a patient. For example, infusion devices must typically be flushed clean after the medication has been dispensed. Sterile saline or occasionally a dextrose solution may be used for this purpose.

In addition, and more importantly for infusion devices using in-dwelling catheterization, once the flow of medication has ceased, the patient's blood may backflow into the infusion system. The blood eventually clots and blocks further flow through the system. For this reason, it is often desirable to maintain a gentle "KVO" (Keep Vein Open) flow of sterile fluid through the infusion system and into the patient, after all of the medication has been delivered. This KVO flow prevents any backflow and clotting. The KVO fluid may also include an anticoagulant such as heparin.

In other instances, it may be desirable to deliver two types of medication to the patient, either simultaneously or sequentially. There is a need for infusion systems having this capability.

A number of past products have been used to deliver a single fluid, such as medication, into a patient at a controlled flow rate. A typical example, which has been quite successful commercially, is illustrated in U.S. Pat. No. 5,080,652 to Sancoff, et al.

The relevant art has tended to focus on ambulatory care concerns. For example, many devices have been developed primarily for use by the patient, enabling him to administer the drug to himself or herself over a prolonged time without a hospital stay.

Devices such as the Sancoff, et al., product have been designed and intended for use shortly after preparation. The devices are filled with medication and soon thereafter connected to the patient, usually through an intravascular tube. The medication is then administered to the patient by the fluid flow and metering components of the particular device. For instance, in the Sancoff, et al. device the medication is delivered by elastic membranes which push the medication into the patient. Other devices, such as the one described in U.S. Pat. No. 5,106,374 to Apperson, et al. use compressed gas to force the medication from a container.

Some devices use chemicals that react to generate gas upon contact, providing on-the-spot pressurization. See, for example, U.S. Pat. No. 3,023,750 to Baron. The Baron device uses generated gas to force liquid from a bag for delivery to a patient.

However, none of these devices incorporate a means for delivering two or more fluids to a patient simultaneously or sequentially. In particular, none of these devices is capable of automatically flushing itself and its downstream intravascular lines clean. And none of these devices is capable of automatically providing a KVO flow of a different fluid, after the first fluid (the medication) has been delivered, to keep the intravascular lines open, or to provide a second liquid medication to the patient either together with or following infusion of a first liquid medication.

Thus, a need exists for a device which can be incorporated into a fluid infusion system to provide a simultaneous or sequential flow of two or more fluids to a patient.

SUMMARY OF THE INVENTION

This invention comprises apparatus and methods for delivering for patient infusion two or more fluids. A remarkable aspect of this invention is that it uses the same fluid displacement system to deliver both the first and successive infusion fluids. Another remarkable feature is that, if desired, it automatically begins the discharge of the next infusion fluid once the preceding infusion fluid has been nearly completely discharged.

A basic apparatus of this invention has a fluid delivery compartment, containing a first infusion fluid; a fluid displacement system, which displaces the first infusion fluid from the fluid delivery compartment; and a fluid container, containing a second infusion fluid, which responds to the fluid displacement system by discharging the second infusion fluid into the fluid delivery compartment when the system has displaced a predetermined amount of the first infusion fluid from the fluid delivery compartment.

A more refined apparatus of this invention employs a flexible membrane as the fluid displacement system. The membrane is driven by gas pressure, generated in a reaction compartment which has two or more chemical reactants which, when combined, react to evolve gas. Alternatively, the fluid can be displaced by gravity, spring forces or elastomeric forces.

In a still more refined embodiment, the fluid container is located within the fluid delivery compartment. The fluid container is preferably a bag, constructed of one or more thin sheets whose edges are sealed to form a closed container. In a preferred embodiment, the bag is composed of a polyolefin or a modified polyolefin.

The fluid container preferably responds to the fluid displacement system by opening when the system has displaced enough fluid. The container may have one or more weak spots induced in it to promote controlled opening. Alternatively, a sharp surface may be located on the fluid displacement system, or elsewhere on the apparatus itself, to provoke opening of the bag when a desired amount of the first infusion fluid has been displaced.

Another embodiment of the invention incorporates a flow restrictor in operable relation to the fluid container. The flow restrictor regulates the discharge of the second infusion fluid from the fluid container.

The "predetermined amount" of the first infusion fluid to be displaced before the fluid container discharges its contents into the fluid delivery compartment may be any fraction of that fluid but is preferably substantially all of the first infusion fluid. The second infusion fluid may be a sterile saline solution, or a sterile dextrose infusion solution, and it can contain an anticoagulant. Alternatively, it can contain a second medication.

A basic method of this invention comprises the steps of providing a fluid delivery compartment containing a first infusion fluid; providing a fluid container containing a second infusion fluid; displacing the first infusion fluid from the fluid delivery compartment; and discharging the second infusion fluid when a predetermined amount of the first infusion fluid has been displaced from the fluid delivery compartment.

A more refined method employs an expanding gas to perform the displacing step by acting on the first infusion fluid through a flexible membrane. Alternatively, gravity can be used to displace the fluid. The discharging step may be performed by opening the fluid container.

Another version of the method further comprises the step of regulating the discharge of the second infusion fluid from the fluid container.

BRIEF DESCRIPTION OF THE DRAWING FIGURES

FIG. 11 is a top view of another preferred embodiment of the device of the present invention.

FIG. 12 is a side view of the device of FIG. 11.

DETAILED DESCRIPTION OF THE PREFERRED EMBODIMENTS

We have invented apparatus and methods to allow the simultaneous or sequential infusion of two or more fluids from an infusion pump. In general, the invention achieves this function through the use of one or more bags containing infusion fluids. The bags burst, discharging their contents either into a main fluid delivery compartment which originally contains and discharges a first infusion fluid, or directly into the tubing connected to the device.

Co-pending U.S. patent applications, Ser. Nos. 08/105,284 and 08/105,327, the disclosures of which we incorporate here by reference, disclose preferred infusion devices which are readily adapted to attainment of this invention. Those devices generally include a housing divided into a liquid reservoir and a gas expansion reservoir by a membrane. The membrane ordinarily extends substantially in the direction of the gas expansion reservoir when the device is filled with a liquid in the liquid reservoir. When gas expands within the gas expansion reservoir, the membrane is pushed in the direction of the liquid reservoir, displacing the liquid. In a preferred embodiment, the gas expansion reservoir is in communication with a gas generation compartment. The compartment separately houses two or more chemicals which together react to evolve gas.

The structural aspects of the devices disclosed in these co-pending applications are particularly suited to modification in accordance with this invention. Appropriate modifications to prior and future devices, to achieve the same result, are also clearly possible. These modifications will become more apparent through reference to the accompanying figures in our discussion below.

Figure 1:
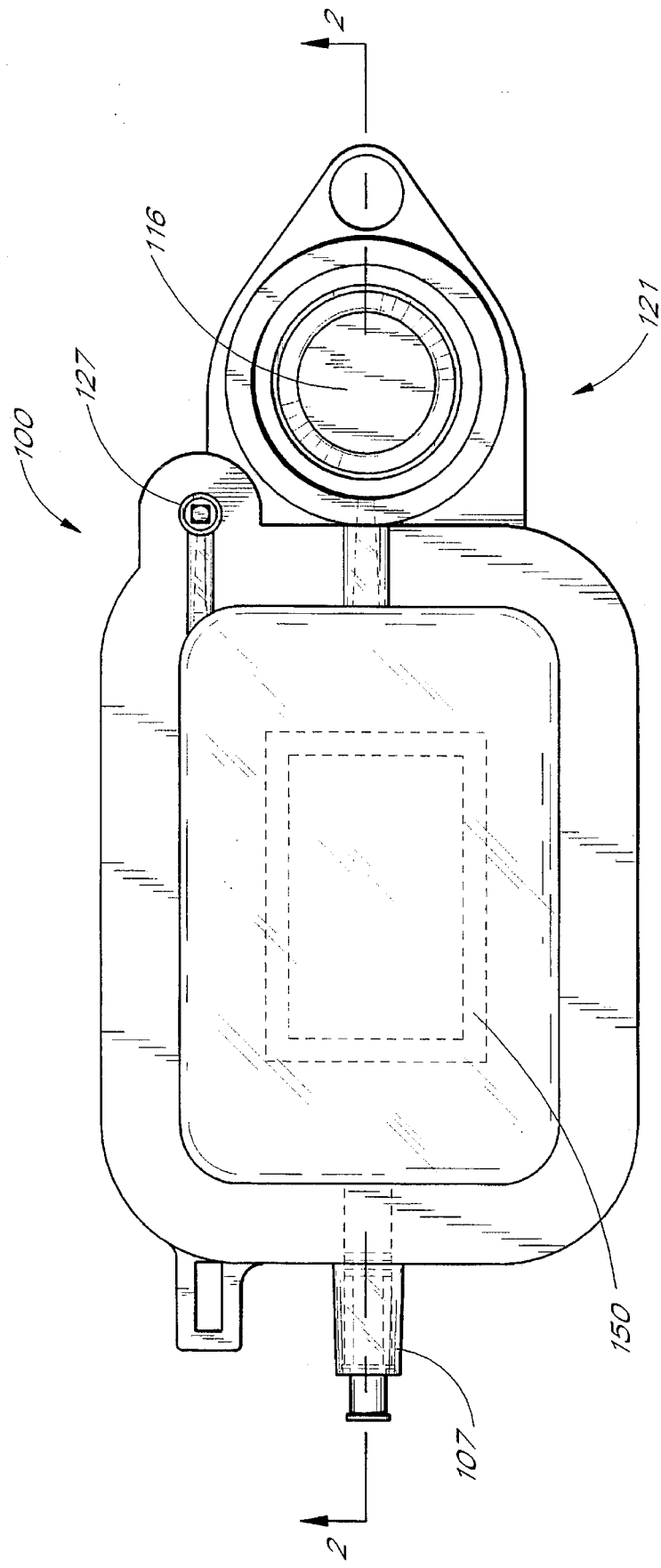
FIG. 1 is a top view of a preferred infusion device of this invention.

FIG. 1 shows the top view of a preferred version of an infusion device. The design and control features of this device are described in detail in the previously referenced applications. For the purposes of this invention, a brief review of this device's design is merited.

Figure 2:
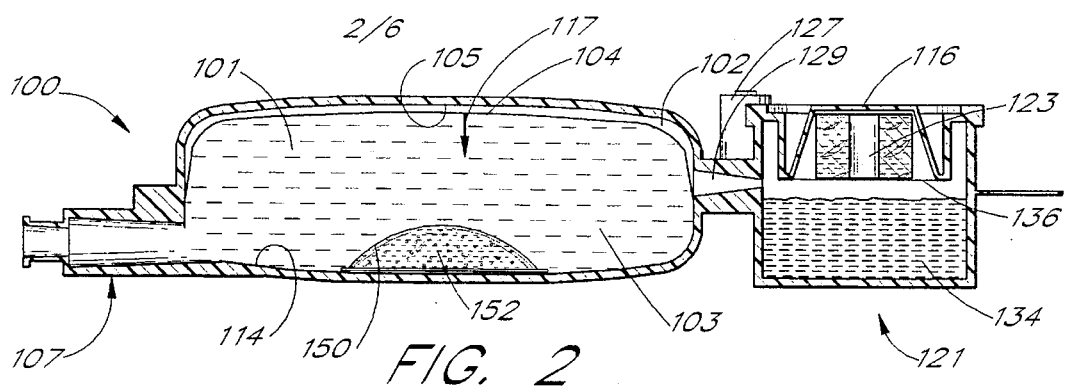
FIG. 2 is a cross-sectional view taken along line 2—2 in FIG. 1.

The device 100 is preferably of generally rectangular shape with rounded edges or corners. FIG. 2, a side view of the same device 100, shows that the device 100 is separated by a flexible membrane 104 into two compartments: a fluid delivery compartment 101, and a gas expansion compartment 102. When filled, the fluid delivery compartment 101 contains a first infusion fluid 103 to be delivered to a patient.

FIG. 2 shows that the flexible membrane 104 is held in proximity to (or distended towards) the upper inner wall 105 of the device 100 by the first infusion fluid 103. The membrane 104 may contact the upper inner wall 105, or be spaced slightly away from it. The region between the membrane 104 and the upper inner wall 105 is a gas expansion compartment 102.

As shown clearly in FIGS. 1 and 2, the first infusion fluid 103 is preferably kept within the fluid delivery compartment 101 by a one-way valve 107. The valve 107 can be specially manufactured, or it can be a standard one-way luer fitting, such as those that are commercially available. The Halkey-Roberts Corporation (St. Petersburg, Fla.) produces a variety of luer syringe check valves that can be used for this purpose. We prefer to use Halkey-Roberts Model No. V24200.

All materials that contact the first infusion fluid 103, such as the flexible membrane 104, the fluid delivery compartment 101, and the valve 107 and its components, should be constructed of materials that are non-leaching and appropriate for medical use. One such material is ultrapure polypropylene, described in U.S. Pat. No. 4,803,102. Thin preparations of ultrapure polypropylene (e.g., 0.002 to 0.010 inch gauge) can be used for the flexible membrane 104. Thicker gauge materials (e.g., molded to 0.030 to 0.060 inch gauge) are preferred for the inner walls 105 and 114.

A gas generating compartment 121 is in fluid communication with the gas expansion compartment 102 through a channel 129 or other conduit. Gas generated in the gas generating compartment 121 will travel through the channel 129, filling the gas expansion compartment 102. Preferably, the device 100 includes a pressure relief valve 127 in fluid communication with the gas expansion compartment 102 which prevents overpressurization of the device 100.

The gas generating compartment 121 includes a depressible membrane 116 which is sealingly joined to the case of the device 100. The depressible membrane 116 sits above the gas generating compartment 121. Inside the gas generating compartment 121 are two or more reactive compositions. Preferably, the first reactant is in the form of a solid 123, and the second reactant is in the form of a liquid 134. The reactants are initially separated by an openable barrier 136. Depressing the membrane 116 causes the solid reactant 123 to contact the liquid reactant 134 and evolve a gas 122, as shown more clearly in FIG. 3.

The flexible membrane 104 is preferably impermeable to the gas 122. Either a gas impermeable material, such as a polyolefin or a modified polyolefin, or a composite or multi-layer membrane, can be used. In the latter case, for example, the surface of the membrane 104 in contact with the first infusion fluid 103 can be prepared from ultrapure polypropylene, as described above, while the surface that contacts the gas 122 can be made of a polyolefin such as a copolymer of polypropylene and polyethylene.

Within the fluid delivery compartment 101 and below the membrane 104 lies an openable bag 150, shown in the bottom half of the device 100 in FIG. 2. The bag 150 is advantageously sealingly joined, preferably by thermal welding, to the lower inner wall 114 of the device. As shown more clearly in FIG. 1, in the preferred embodiment the bag 150 is welded at its corners to the lower inner wall 114. It may alternatively be welded along each of its edges or may comprise a separate, self contained bag. The openable bag 150 contains a second infusion fluid 152. In a preferred embodiment, the interior of the bag is accessible from the outside of the device, to allow the user to select the desired fluid and fill the bag prior to infusion.

The bag 150 preferably should be made of a flexible, yet not particularly pliant material, because it must deform a predetermined amount and then open. A polyolefin, such as polypropylene, or more preferably a copolymer of polyethylene and polypropylene, is ideally suited to this task. Because the infusion device 100 may be sterilized by autoclaving, the bag 150 (and all other components of the device) is advantageously made of a material capable of withstanding the heat and pressure of this process, and therefore is preferably not made of polyethylene alone. In addition, in the preferred embodiment of this invention, the wall 114 is constructed of polypropylene, and therefore the bag 150 may be made of a material having at least some polypropylene content: like materials tend to thermally weld together better than unlike materials. Finally, in contrast to the flexible membrane 104 which must be gas impermeable, there is no need for the openable bag 150 to have more than a single layer.

The bag 150 can be created by thermally welding together the four edges, and three of the four corners, of two rectangular sheets of polyolefin material, forming a generally rectangular bag with an open hole at one corner. The second infusion fluid 152 may be injected into the bag 150 at the open corner; that corner is then thermally welded shut.

Figure 10:
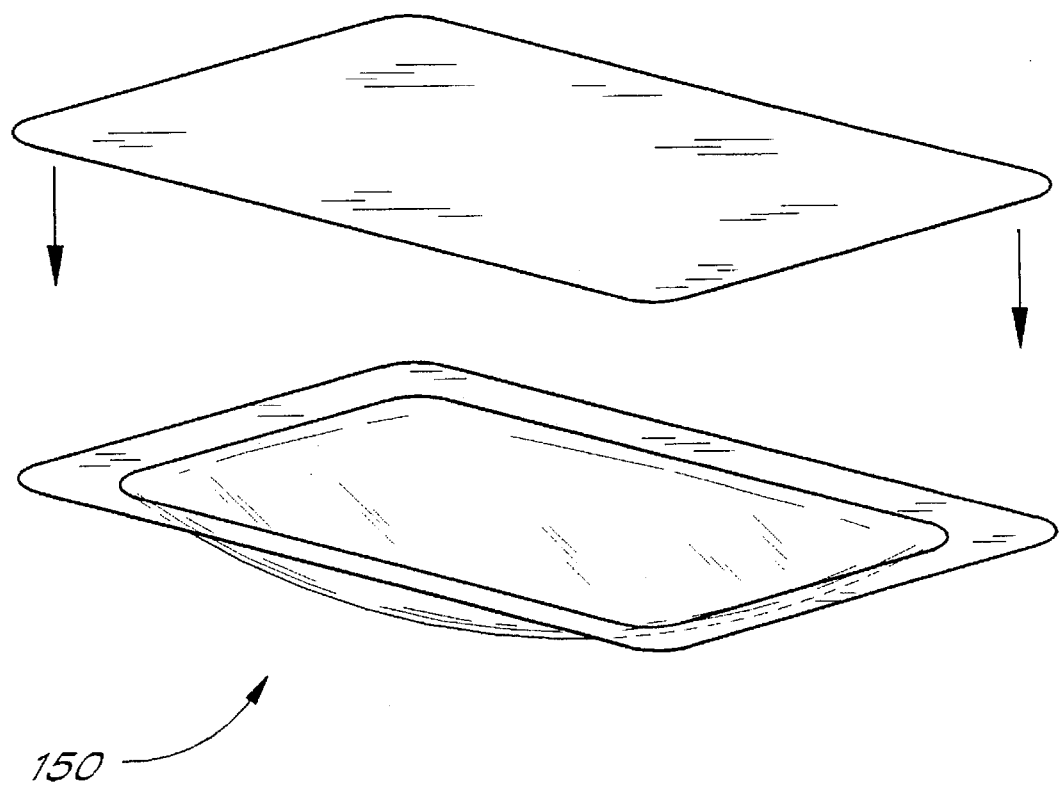
FIG. 10 is a perspective view of the two halves of the preferred bag, showing its manufacture by the form-fill-seal process.

Alternatively, and preferably, the openable bag 150 is created by a form-fill-seal process, illustrated by FIG. 10. In this process, one generally rectangular sheet of polyolefin material is vacuum formed into a shallow cupped basin, and then filled with the second infusion fluid 152. A second sheet of polyolefin material is then placed over the top of the basin formed by the first sheet, and the two sheets are thermally welded together, forming a continuous seal around their periphery.

Because any gas trapped inside the openable bag 150 could be released later and enter the patient, causing a gas embolism, any process for creating the bag 150 must be carefully controlled to prevent, or at least drastically minimize, any gas (such as air) from becoming trapped inside the bag 150 after it is filled and sealed.

Figure 3:
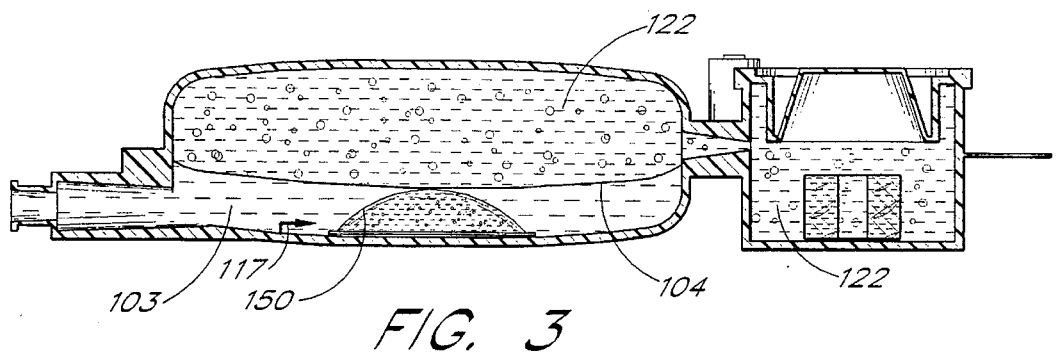
FIG. 3 is the cross-sectional view shown in FIG. 2 demonstrating the operation of this invention, as the flexible membrane in the device displaces the first infusion fluid, and simultaneously approaches the bag containing the second infusion fluid.
Figure 4:
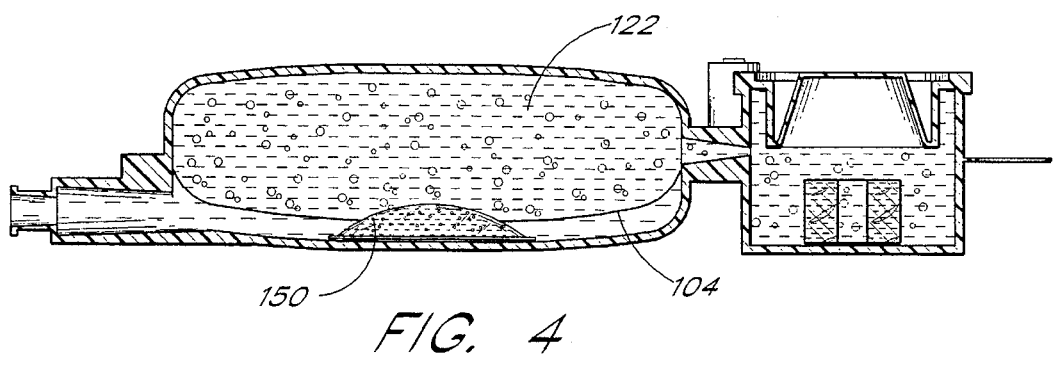
FIG. 4 is the cross-sectional view shown in FIG. 3 demonstrating the operation of this invention, as the membrane compresses the bag and its contents.
Figure 5:
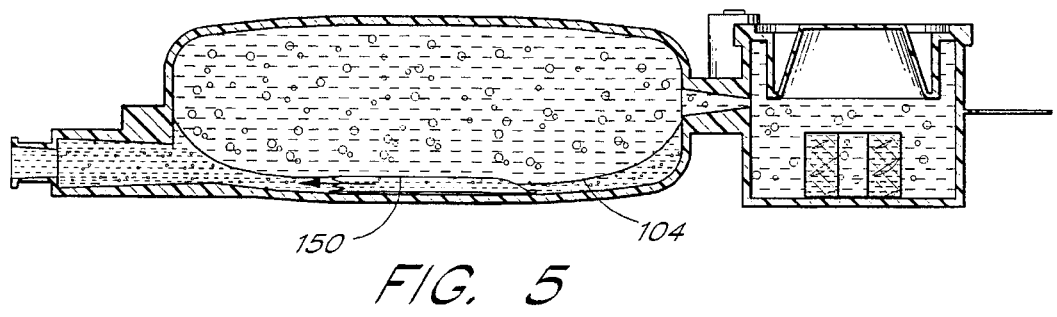
FIG. 5 is the cross-sectional view shown in FIG. 3 demonstrating the operation of this invention, as the membrane expels the contents of the bag, causing the second infusion fluid to be displaced from the device.

The operation of the device 100 of the present invention is shown in FIGS. 3 through 5. As shown in FIG. 3, the gas generating reaction will cause the gas expansion compartment 102 to expand, displacing the fluid 103 from the fluid delivery compartment 101. Eventually, the flexible membrane 104 will contact the openable bag 150, forcing it toward the lower inner wall 114. FIG. 4 shows the bag 150 deforming, but not opening, under pressure from the membrane 104. As shown in FIG. 5, as the bag 150 experiences internal pressure caused by pressure on the membrane 104, the bag 150 will ultimately burst and expel the second infusion fluid 152. The second infusion fluid 152 is then displaced from the fluid delivery compartment 101.

In an alternative embodiment, the fluids are driven from the container by pressure created by gravity. This can be accomplished by orienting the device such that gravity causes the first liquid to be expelled and causes the bag containing the second fluid to discharge its contents. Alternatively, spring or elastomeric forces can also be used to drive the fluid from the container.

In another alternative embodiment of the device 100, the surface of the membrane 104 is fitted with a sharp penetrating or tearing device, such as a spike or barb 117, which facilitates bursting of the bag 150. The barb 117 can be placed on the inside surface of the flexible membrane 104 above the bag 150, as illustrated in FIG. 2. As the gas expansion compartment 102 expands, the barb 117 contacts the bag 150 causing it to open. Alternatively, as illustrated in FIG. 3, the barb 117 can be located adjacent the bag 150, such that as the bag 117 is deformed under increasing pressure, the surface of the bag contacts the barb 117 and bursts.

Figure 6:
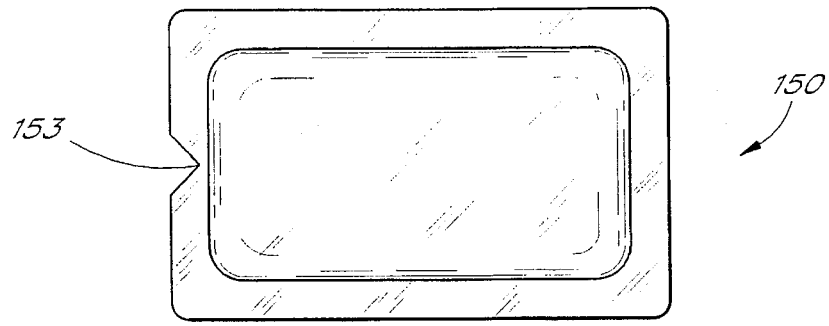
FIG. 6 is a top view of one version of the bag, showing a notched weakening in its peripheral seal which controls the direction and timing of its opening.
Figure 7:
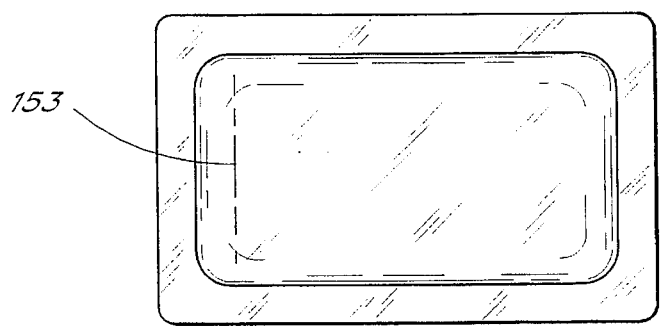
FIG. 7 is a top view of another version of the bag, showing a scored weakening on its surface which controls the direction and timing of its opening.
Figure 8:
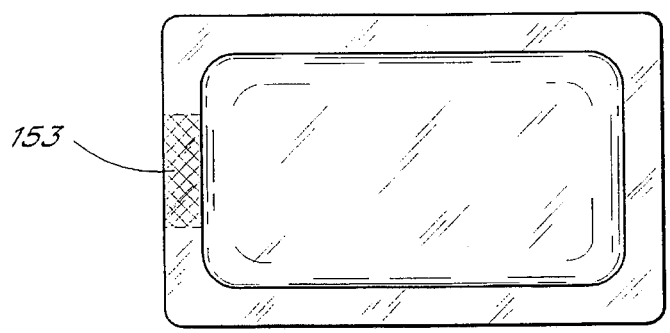
FIG. 8 is a top view of another version of the bag, showing a strip or coating inserted between its sealed layers, weakening the seal to control the direction and timing of its opening.

Because the bag 150 is intended to open under pressure, one or more weak spots 153 may be induced into it. These weak spots 153 may be created by, for example, notching the sealed edge of the bag 150 as shown in FIG. 6; scoring or otherwise thinning the bag's 150 surface as shown in FIGURE 7; or introducing a strip or coating of a second material between the sealed layers at one edge of the bag 150 as shown in FIG. 8.

In another embodiment, a spike or other sharp surface (not shown) may be placed in close relation to the bag 150, such that when the bag 150 is deformed by the flexible membrane 104, it eventually impinges on the spike, which causes it to burst. We contemplate that such a spike may be placed advantageously within the one-way valve 107, and by suitable arrangement of the membrane 104 and bag 150 the bag 150 can be made to drive against the spike by pressure from the membrane 104.

In yet another preferred embodiment of the present invention, illustrated in FIGS. 11 and 12, the openable bag 160 has a neck portion 163 which extends into the neck 165 of the device 100. The neck 163 of the bag 160 ends in a frangible seal 167. The neck 163 of the bag 160 and the frangible seal 167 are disposed within the neck 165 of the device 100, such that they are not compressed by the flexible membrane 104 in response to increasing pressure in the gas expansion compartment 102. The flow of the first fluid 103 out of the device 100 is typically controlled by a downstream flow controller of conventional design (not shown). As long as the first liquid is present, the laws of hydraulics dictate that the pressure in the neck 163 is the same as in the main body of the bag 160. Once the first fluid 103 has been displaced from the device 100, the downstream flow controller no longer provides back pressure in the device, thus, the ambient pressure of the membrane 104 against the main body of the bag 160 is greater than the pressure on the neck 163. This pressure difference between the neck 163 of the bag 160 and the main body of the bag 160 results in the seal 167 rupturing and the contents of the bag 160 flowing from the device 100.

In the preferred embodiment, the volume enclosed by the openable bag is approximately 20 ml. This volume is typically sufficient to flush clean the retained volume of the downstream intravascular apparatus, which is approximately 2 to 4 ml. When used to flush the intravenous lines after delivery of the first infusion fluid, the second infusion fluid is preferably sterile saline, or possibly a sterile dextrose solution. Where KVO (Keep Vein Open) flow is desired, the second infusion fluid may also include an anticoagulant such as heparin. When used to deliver a second fluid simultaneously with the first, the fluid can be any medication in liquid form.

Figure 9:
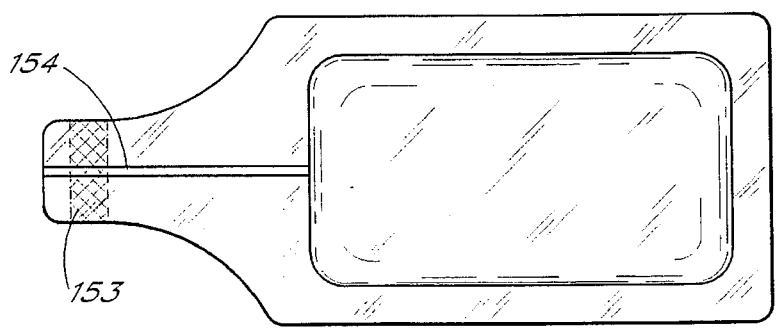
FIG. 9 is a top view of a version of the bag which includes an integral flow-limiting device to restrict the flow rate of the second infusion fluid as it exits the bag.
Figure 13:
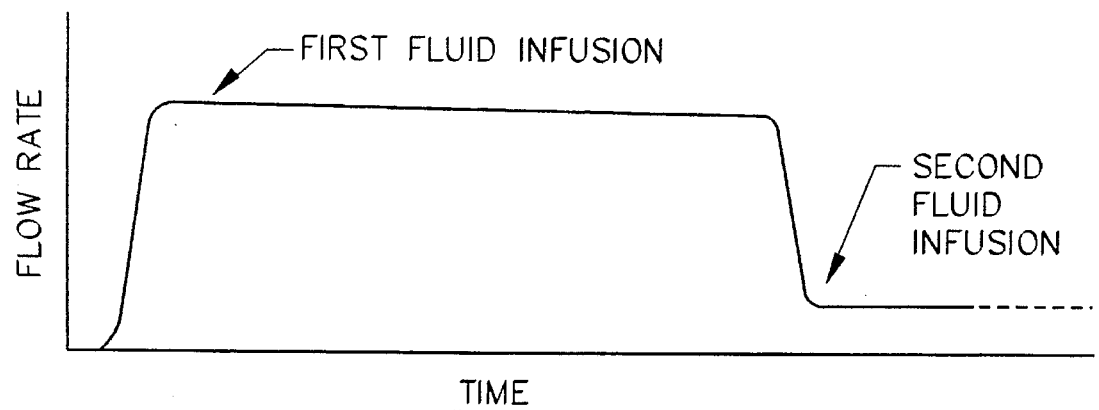
FIG. 13 is a graph depicting the flow rate of the device which includes an integral flow-limiting device as illustrated in FIG. 9.

Because it is often desirable to maintain KVO flow for a considerable time after the first infusion fluid 103 has been delivered, a flow-limiting device 154, such as a small tube or orifice into which the openable bag 150 bursts (the direction of its burst controlled by the introduction of a frangible seal 167 or weak spot 153, as noted previously) may be incorporated into the device 100. FIG. 9 shows one embodiment of such a flow-limiting device 154 which may be incorporated into the openable bag 150. The flow-limiting device 154 would restrict the exiting flow rate of the second infusion fluid 152 from the bag 150, extending the duration of its delivery into the patient. A graph illustrating exemplary flow rates of the two infusion fluids in this embodiment of the device is shown in FIG. 13. Alternatively, the flow limiting device 154 may be used without bursting the bag 150 to prolong flow of the second infusion fluid 152 until long after the first infusion fluid 103 is gone.

In operation, the user attaches the device's one-way valve 107 to, for example, a sterile tube leading to an intravascular catheter (not shown). If necessary, the user may add medication to the first infusion fluid 103 already present in the pump 100.

The user then depresses the membrane 116, causing the openable barrier 136 to open and the solid reactant 123 to contact the liquid reactant 134 in the gas generation compartment 121, evolving a gas 122. The gas 122 fills the gas expansion compartment 102, forcing the membrane 104 to move into the fluid delivery compartment 101. This action of the membrane 104 displaces the first infusion fluid 103, causing the first infusion fluid 103 to flow into the tubing. Once positive flow has been established through the tubing, the intravascular catheter can be connected safely to the patient.

After substantially all of the first infusion fluid 103 has been delivered to the patient, the pressure of the membrane 104 on the bag 150 will cause the bag 150 to open, expelling the second infusion fluid 152 into the fluid delivery compartment 101. Continued movement of the membrane 104 in response to further pressure from the gas 122 then displaces the second infusion fluid 152, causing the second infusion fluid 152 to flow into the tubing.

The operation of the second preferred embodiment of the device of the present invention, illustrated in FIGS. 11 and 12, is similar to that just described. After the device 100 is attached to sterile tubing, the user depresses the membrane 116, opening the openable barrier 136 and causing the solid reactant 123 and liquid reactant 134 to contact each other and generate gas. The gas fills the gas expansion compartment 102, causing the membrane 104 to expand in the direction of the fluid delivery compartment 101. Once the first fluid 103 is gone, the pressure of the membrane 104 on the main body of the openable bag 160 is greater than the pressure on the neck 163 of the bag 160. Therefore, a pressure differential is created between the neck 163 and main body of the bag 160. This pressure differential causes the seal 167 in the neck of the bag 163 to open, and fluid to flow from within the body of the bag 160. Alternatively, by eliminating the seal 167 (and optionally substituting a flow limiting device 154), the fluids in the fluid delivery compartment 101 and the openable bag 160 can be administered simultaneously from the device 100.

Clearly many other embodiments of this device may exist which, while not expressly described above, are within the scope and spirit of this invention. For example, the openable bag 150 may be incorporated into other types of fluid delivery systems in such a manner that the bag 150 will open and release a second infusion fluid 152 into the main fluid delivery stream. These other fluid delivery systems may use, for example, gas- or spring-driven pistons or plungers instead of the flexible membrane disclosed above. The Baron device mentioned previously uses a cuff-like apparatus to squeeze fluid from an infusion bag. Any of these or other fluid delivery systems may be fitted with a bag 150 in the scope of this invention, thus effecting the simultaneous or sequential delivery of a second infusion fluid. Additionally, two or more bags 150 may be suitably arranged so that they will simultaneously or sequentially burst or open under continued pressure, effecting the simultaneous or sequential delivery of three or more infusion fluids.

In addition, it should be appreciated that the concept of the present invention is broadly applicable to fluid delivery in general. For example, the sequential fluid delivery structure described in connection with an infusion device and method may be readily adapted for other types of fluid delivery in industry, agriculture, recreation, and home use. Thus, we intend our earlier description to be illustrative only. Our invention is to be limited only by the following claims.

We claim:

1. An apparatus for delivering two or more fluids, said apparatus comprising:

a fluid delivery compartment, containing a first fluid;

a fluid displacement system, which exerts a force on said fluid delivery compartment and displaces said first fluid from said fluid delivery compartment; and a fluid container containing a second fluid, located within said fluid delivery compartment and responsive to said force exerted by said fluid displacement system, which discharges said second fluid when said fluid displacement system has displaced a predetermined amount of said first fluid from said fluid deliver compartment.

2. The apparatus of claim 1, wherein said fluid displacement system comprises a flexible membrane adjacent said first fluid.

3. The apparatus of claim 2, wherein said flexible membrane is driven by pressure from a source of gas.

4. The apparatus of claim 3, wherein said source of gas is a gas reaction compartment having two or more reactants which combine to evolve gas.

5. The apparatus of claim 1, wherein said fluid displacement system comprises a force selected from the group consisting of gravity, spring force and elastomeric force.

6. The apparatus of claim 1, wherein said fluid container is a bag.

7. The apparatus of claim 1, wherein said fluid container is comprised of one or more sheets of material, said sheets having edges and sealed at said edges to form a closed container.

8. The apparatus of claim 1, wherein said fluid container is comprised of a polyolefin or a modified polyolefin.

9. The apparatus of claim 1, wherein said fluid container has one or more weak spots at which it opens when said fluid displacement system has displaced a predetermined amount of said first infusion fluid from said fluid delivery compartment.

10. The apparatus of claim 1, wherein said apparatus further comprises a sharp surface which opens said fluid container when said fluid displacement system has displaced a predetermined amount of said first fluid from said fluid delivery compartment.

11. The apparatus of claim 1, wherein said fluid displacement system further comprises a sharp surface which opens said fluid container when said fluid displacement system has displaced a predetermined amount of said first fluid from said fluid delivery compartment.

12. The apparatus of claim 1, wherein said apparatus further comprises a flow restrictor located in operable relation to said fluid container, which regulates the discharge of said second fluid from said fluid container.

13. The apparatus of claim 1, wherein said fluid container further comprises a flow restrictor located in operable relation to said fluid container, which regulates the discharge of said second fluid from said fluid container.

14. The apparatus of claim 1, wherein said predetermined amount of said first fluid is substantially all of said first fluid.

15. The apparatus of claim 1, wherein said second fluid is selected from the group consisting of a sterile saline infusion solution and a sterile dextrose infusion solution.

16. The apparatus of claim 1, wherein said second fluid contains an anticoagulant.

17. A method for delivering for patient infusion two or more fluids, said method comprising the steps of:

providing a fluid delivery compartment containing a first infusion fluid and containing at least one fluid container containing a second infusion fluid therein;

displacing said first infusion fluid from said fluid delivery compartment through an exit port; and discharging said second infusion fluid through said exit port when a predetermined amount of said first infusion fluid has been displaced from said fluid delivery compartment or simultaneously with discharge of at least a portion of said first infusion fluid.

18. The method of claim 17, wherein said displacing step is performed by acting on said first infusion fluid through a flexible membrane.

19. The method of claim 18, wherein said acting step is performed by an expanding gas.

20. The method of claim 17, wherein said displacing and discharging steps are performed by gravity, spring or elastomeric forces acting on said first and second infusion fluids.

21. The method of claim 17, wherein said discharging step is performed by opening said fluid container.

22. The method of claim 17, further comprising the step of restricting the discharge of said second infusion fluid.

23. The method of claim 17, wherein one portion of said second infusion fluid is discharged with at least a portion of said first infusion fluid, and another portion of said second infusion fluid is discharged after discharge of said first infusion fluid.

* * * * *